United States Patent
Parihar et al.

(10) Patent No.: US 8,162,850 B2
(45) Date of Patent: Apr. 24, 2012

(54) HAND ACTUATED TETHERLESS BIOPSY DEVICE WITH SCISSORS GRIP

(75) Inventors: Shailendra K. Parihar, Mason, OH (US); Michael J. Andreyko, Cincinnati, OH (US); Eric B. Smith, Cincinnati, OH (US); James Janszen, Cleves, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 401 days.

(21) Appl. No.: 12/335,632

(22) Filed: Dec. 16, 2008

(65) Prior Publication Data

US 2010/0152611 A1  Jun. 17, 2010

(51) Int. Cl.
 *A61B 10/00* (2006.01)
 *A61B 17/32* (2006.01)
 *A61B 17/14* (2006.01)

(52) U.S. Cl. ........ 600/565; 600/562; 600/564; 600/566; 600/567; 606/167; 606/168; 606/170; 606/171; 606/180

(58) Field of Classification Search .......... 600/562, 600/564, 565, 566, 567; 606/167, 168, 170, 606/171, 174, 180, 184, 185
See application file for complete search history.

(56) References Cited

U.S. PATENT DOCUMENTS

| | | | | |
|---|---|---|---|---|
| 3,561,429 A * | 2/1971 | Jewett et al. | | 600/565 |
| 5,213,110 A * | 5/1993 | Kedem et al. | | 600/567 |
| 5,335,672 A * | 8/1994 | Bennett | | 600/567 |
| 5,511,556 A * | 4/1996 | DeSantis | | 600/567 |
| 5,526,822 A | 6/1996 | Burbank et al. | | |
| 5,649,547 A * | 7/1997 | Ritchart et al. | | 600/566 |
| 6,086,544 A | 7/2000 | Hibner et al. | | |
| 6,251,121 B1 * | 6/2001 | Saadat | | 606/180 |
| 6,626,849 B2 | 9/2003 | Huitema et al. | | |
| 6,758,824 B1 * | 7/2004 | Miller et al. | | 600/568 |
| 7,442,171 B2 | 10/2008 | Stephens et al. | | |
| 7,470,237 B2 * | 12/2008 | Beckman et al. | | 600/564 |
| 7,534,234 B2 * | 5/2009 | Fojtik | | 604/223 |

(Continued)

FOREIGN PATENT DOCUMENTS

EP  1 093 757  4/2001

(Continued)

OTHER PUBLICATIONS

U.S. Appl. No. 60/869,736, filed Dec. 13, 2006, Ritchie et al.

(Continued)

*Primary Examiner* — Max Hindenburg
*Assistant Examiner* — Devin Henson
(74) *Attorney, Agent, or Firm* — Frost Brown Todd LLC

(57) ABSTRACT

A biopsy device includes a body having a cannula, a cutter positioned at least partly within the cannula, a tissue collection chamber, and a vacuum source. In one example, the biopsy device includes a cutter loader for rotating the cutter into a loaded position (e.g., open position). A trigger is engaged with a portion of the cutter loader and may be activated to allow the cutter to rotate back to a closed position. During this rotation, the cutter severs a tissue sample, which may thereafter be drawn through the cutter lumen into the tissue collection chamber under the influence of a vacuum created by the vacuum source. The vacuum source includes a piston configured to be operated by squeezing a scissors grip. A user may apply a single stroke or successive strokes to the piston to produce the vacuum.

20 Claims, 13 Drawing Sheets

U.S. PATENT DOCUMENTS

| | | | |
|---|---|---|---|
| 2007/0032742 A1 | 2/2007 | Monson et al. | |
| 2007/0149894 A1 | 6/2007 | Heske et al. | |
| 2007/0239067 A1* | 10/2007 | Hibner et al. | 600/567 |
| 2008/0195066 A1 | 8/2008 | Speeg et al. | |
| 2008/0214955 A1 | 9/2008 | Speeg et al. | |

FOREIGN PATENT DOCUMENTS

| | | |
|---|---|---|
| EP | 1 832 234 | 9/2007 |
| WO | WO 2008/106583 | 9/2008 |

OTHER PUBLICATIONS

U.S. Appl. No. 60/874,792, filed Dec. 13, 2006, Hibner et al.

International Preliminary Report on Patentability dated Jun. 21, 2011 for Application No. PCT/US2009/067143.

International Search Report dated Mar. 16, 2010 for Application No. PCT/US2009/067143.

* cited by examiner

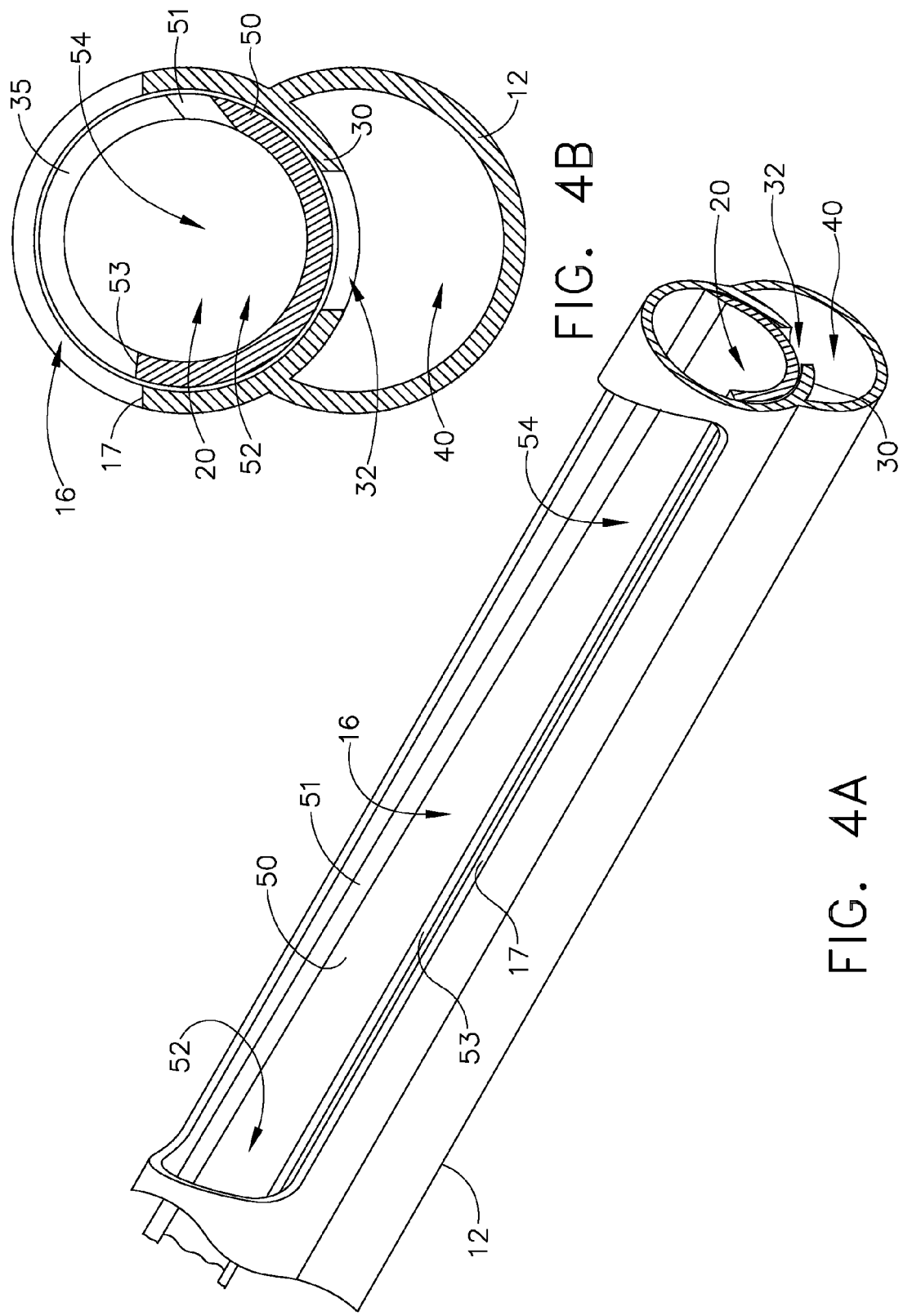

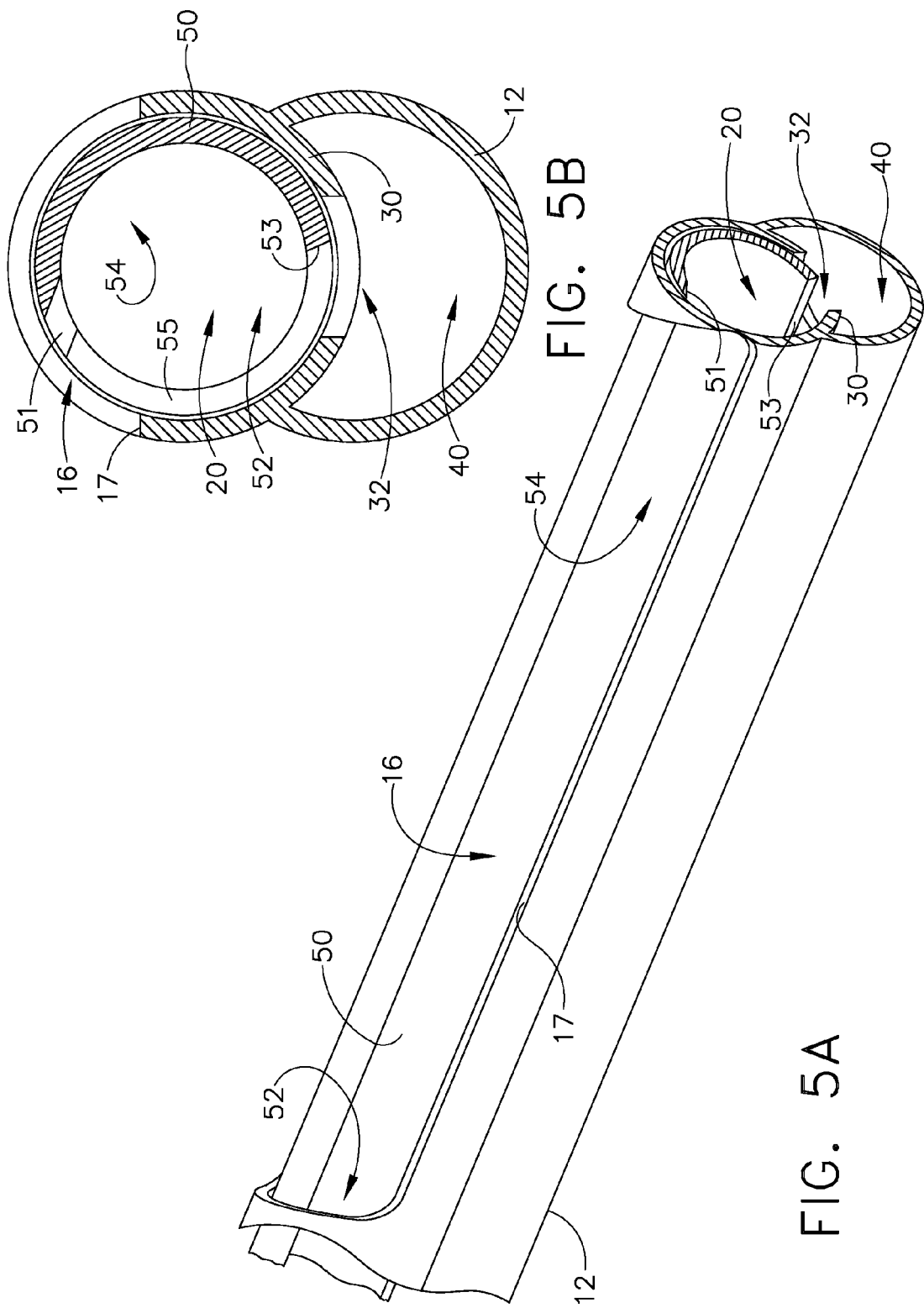

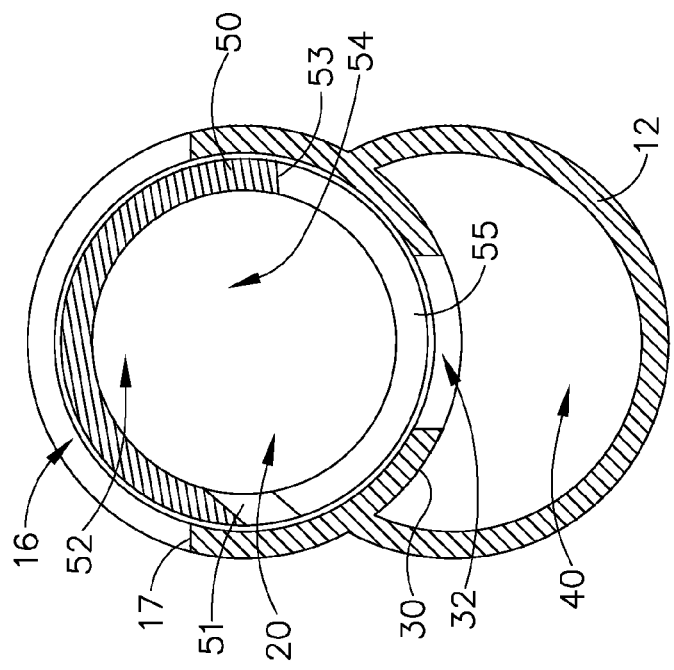
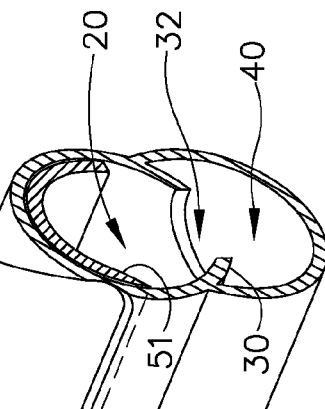
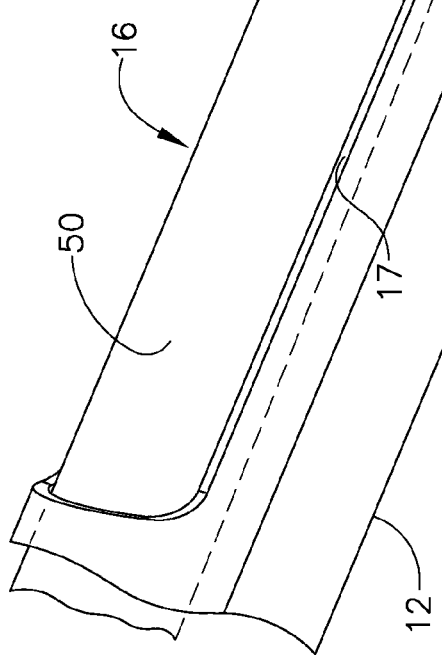

HAND ACTUATED TETHERLESS BIOPSY DEVICE WITH SCISSORS GRIP

BACKGROUND

Biopsy samples have been obtained in a variety of ways in various medical procedures using a variety of devices. Biopsy devices may be used under stereotactic guidance, ultrasound guidance, MRI guidance, or otherwise. Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," filed Nov. 20, 2007; U.S. Provisional Patent Application Ser. No. 60/869,736, entitled "Biopsy System," filed Dec. 13, 2006; and U.S. Provisional Patent Application Ser. No. 60/874,792, entitled "Biopsy Sample Storage," filed Dec. 13, 2006. The disclosure of each of the above-cited U.S. patents, U.S. patent application Publications, and U.S. Provisional patent applications is incorporated by reference herein. While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 4A is a partial perspective view of the cutter and needle of the biopsy device of FIG. 1, with the cutter in a cocked position;

FIG. 4B is an end view of the cutter and needle of the biopsy device of FIG. 1, with the cutter in a cocked position;

FIG. 5A is a partial perspective view of the cutter and needle of the biopsy device of FIG. 1, with the cutter in a firing position;

FIG. 5B is an end view of the cutter and needle of the biopsy device of FIG. 1, with the cutter in a firing position;

FIG. 6A is a partial perspective view of the cutter and needle of the biopsy device of FIG. 1, with the cutter in a fired position;

FIG. 6B is an end view of the cutter and needle of the biopsy device of FIG. 1, with the cutter in a fired position;

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

As shown in FIGS. 1-12, an exemplary biopsy device (2) includes a body (4) connected to a needle portion (10). Body (4) includes a left and right housing. Biopsy device (2) is operable to sever a tissue sample from within a patient and communicate the tissue sample to a location external to the patient. It will be appreciated that the terms "proximal" and "distal" are used herein with reference to a clinician gripping a handle (160) of biopsy device (2). It will be further appreciated that for convenience and clarity, spatial terms such as "right", "left", "vertical" and "horizontal" are used herein with respect to the drawings.

However, surgical instruments are used in many orientations and positions, and these terms are not intended to be limiting or absolute.

I. Exemplary Needle

Figure 1:
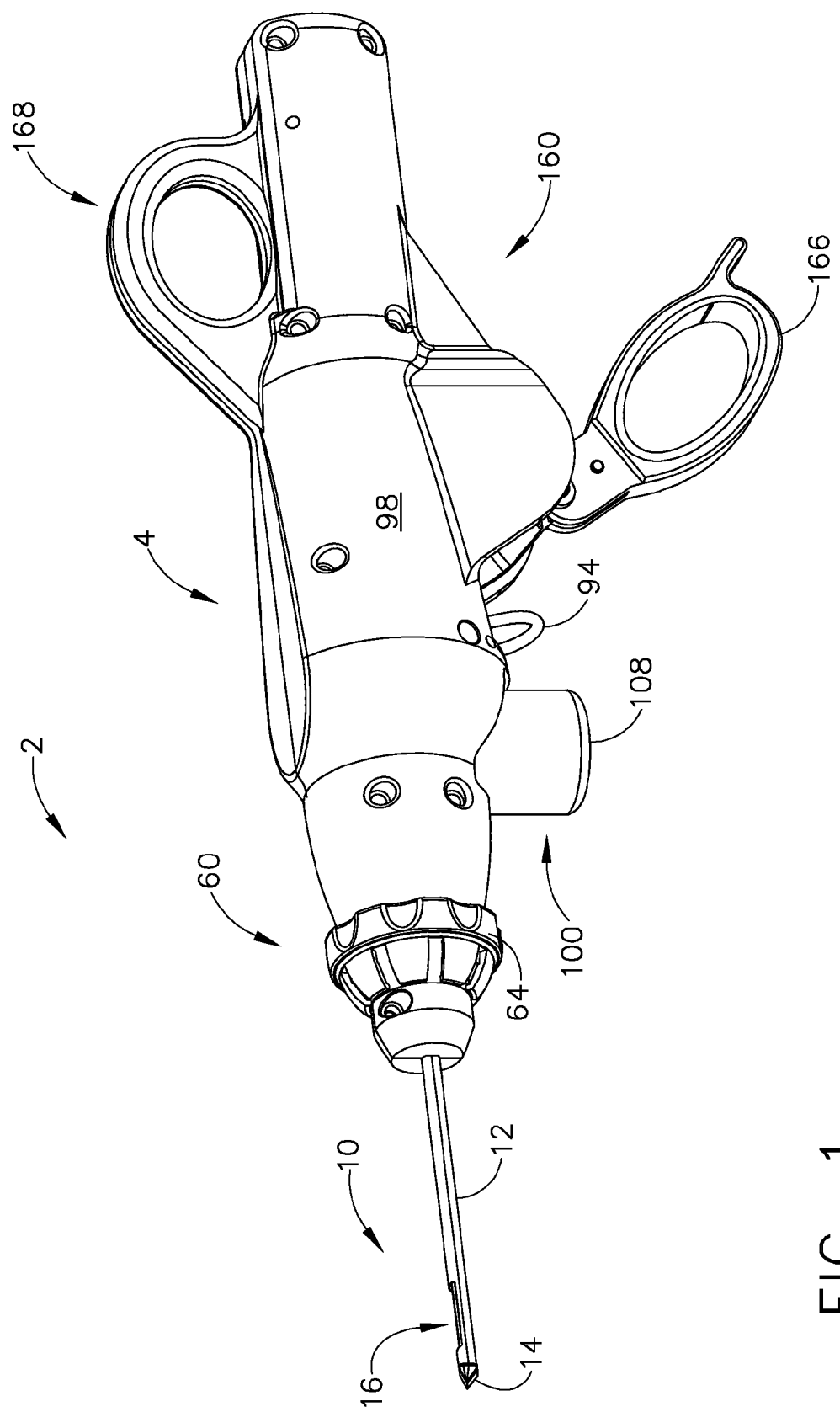
FIG. 1 is a perspective view of an exemplary biopsy device.
Figure 2:
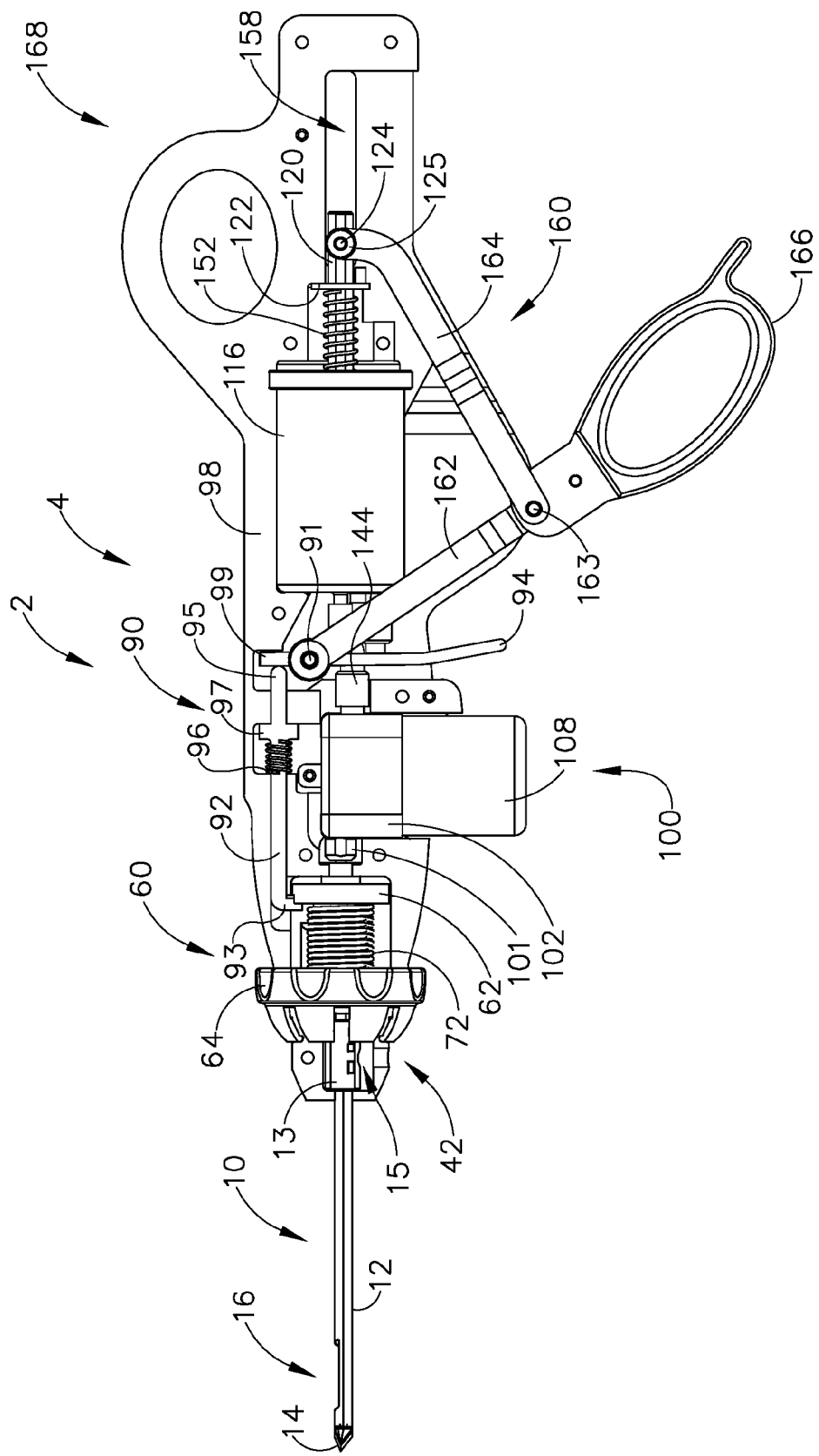
FIG. 2 is a side view of the biopsy device of FIG. 1, with a side housing removed.
Figure 3:
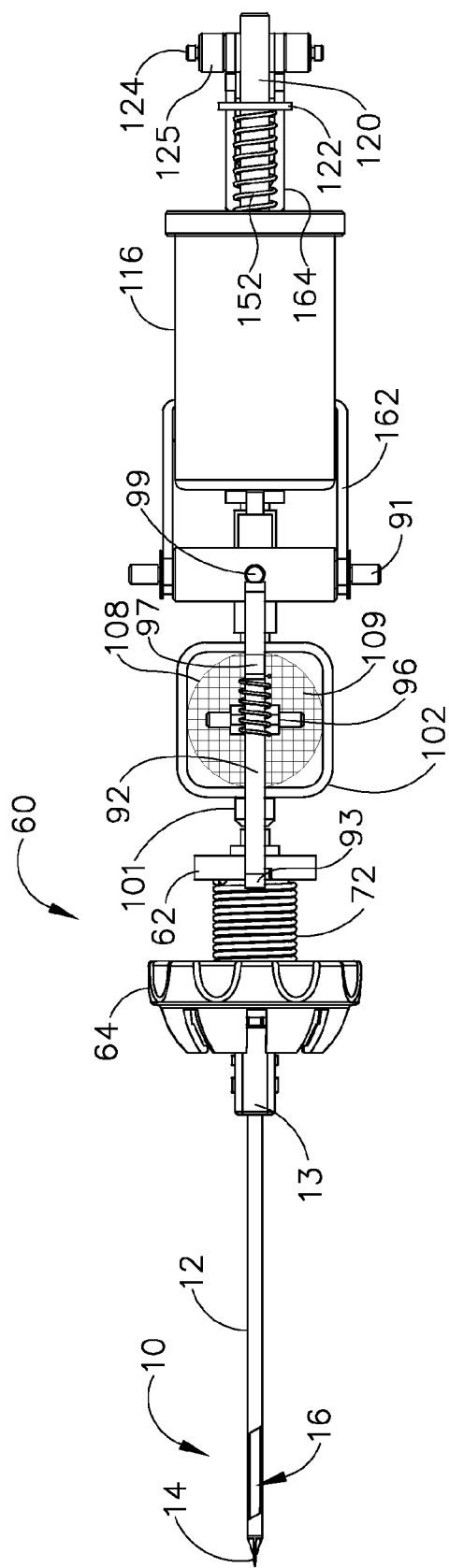
FIG. 3 is a top view of internal components of the biopsy device of FIG. 1.

In the present example and as shown in FIGS. 1-3, needle portion (10) comprises a cannula (12) having a tissue piercing tip (14) and a transverse tissue receiving aperture (16) located proximally from the tissue piercing tip (14). Tissue piercing tip (14) is configured to penetrate tissue without requiring a high amount of force, and without requiring an opening to be preformed in the tissue prior to insertion of tip (14). Suitable configurations for tissue piercing tip (14) will be apparent to those of ordinary skill in the art in view of the teachings herein. For instance, examples of suitable tissue piercing tips are disclosed in U.S. Pub. No. 2008/0214955, entitled "Presentation of Biopsy Sample by Biopsy Device," published Sep. 4, 2008, the disclosure of which is incorporated by reference herein. Still other ways in which tip (14) may be formed, including alternative techniques, materials, and configurations, will be apparent to those of ordinary skill in the art in view of the teachings herein.

As shown in FIGS. 4A-6B, the interior of cannula (12) of the present example defines a cannula lumen (20) and a vent lumen (40), with a divider wall (30) separating the cannula lumen (20) from the vent lumen (40). At least one opening (32) is formed through divider (30) to provide fluid communication between cannula lumen (20) and vent lumen (40). Vacuum, saline, atmospheric air, and/or pressurized air may be communicated from vent lumen (40) to cannula lumen (20) (or vice versa) via opening (32), as will be described in greater detail below.

A shearing edge (17) extends along the length of aperture (16), and is configured to cooperate with a sharp longitudinal edge (51) of a cutter (50) as will be described in greater detail below.

As shown in FIGS. 2-3 and 8-9, the proximal end of cannula (12) terminates in a manifold (13). When biopsy device (2) is fully assembled, as shown in FIG. 1, manifold (13) is obscured within body (4). Manifold (13) substantially seals cannula lumen (20) relative to the atmosphere; while providing a vent (15) to vent lumen (40). In particular, vent (15) of manifold (13) opens into body (4). Body (4) defines an opening (42) near manifold (13), such that vent (15) in manifold (13) is in fluid communication with opening (42) in body (4). With opening (42) being in fluid communication with atmospheric air, vent lumen (40) is thus in fluid communication with atmospheric air via vent (15) and opening (42) in this example. In some versions, a two-way valve (not shown) is mounted at opening (42) and may be closed to prevent venting of vent lumen (40). This two-way valve may be opened when tissue is severed by cutter (50) as described herein, to vent the vent lumen (40) to provide a pressured gradient to transfer severed tissue proximally through cutter lumen (52) (e.g., where vacuum is provided through cutter lumen (52) proximal to the tissue sample). Such a valve may be mounted directly on opening (42), may have a barb connection for a flexible tube then mounted on a flexible tube that is coupled with opening (42), or may have any other suitable configuration or position.

While opening (42) is used in the present example to provide venting to atmospheric air, it should be understood that opening (42) may alternatively be used to communicate vacuum, saline, and/or pressurized air to vent lumen (40). Any suitable technique, structure or apparatus may be used to communicate with vent lumen (40)—via opening (42) or otherwise. Examples of suitable features, components, configurations, and techniques that may be used to communicate vacuum, saline, and/or pressurized air to vent lumen (40) are disclosed in U.S. Pub. No. 2008/0214955, entitled "Presentation of Biopsy Sample by Biopsy Device," published Sep. 4, 2008, the disclosure of which is incorporated by reference herein. Furthermore, a plurality of external openings (not shown) may also be formed in outer cannula (12), and be in fluid communication with vent lumen (40). Examples of such optional external openings are disclosed in U.S. Pub. No. 2007/0032742, entitled "Biopsy Device with Vacuum Assisted Bleeding Control," published Feb. 8, 2007, the disclosure of which is incorporated by reference herein.

Figure 13:
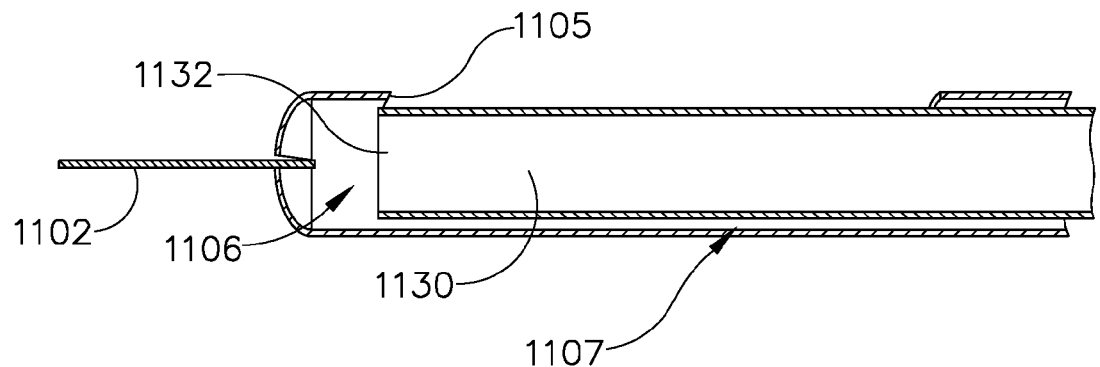
FIG. 13 is a side cross-sectional view of an exemplary alternative needle portion.
Figure 14:
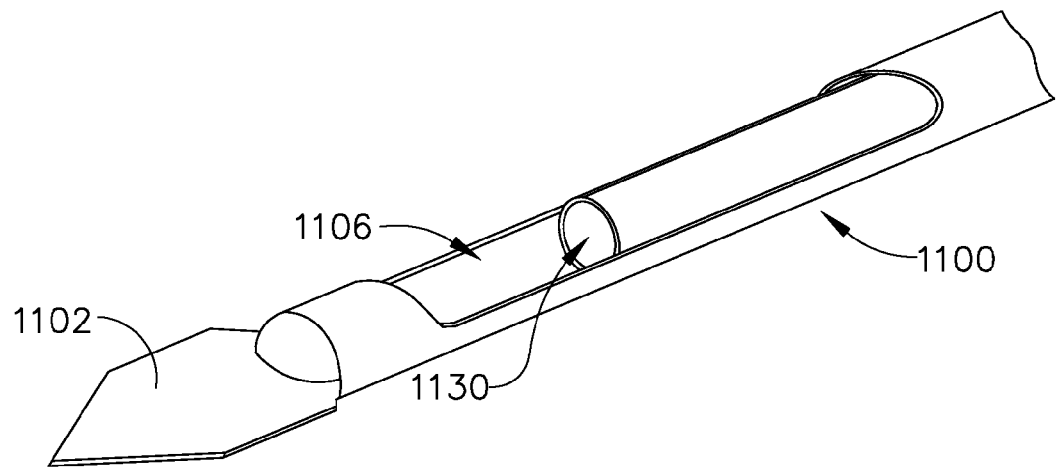
FIG. 14 is a perspective view of the needle portion of FIG. 13.

An exemplary alternative needle portion (1100) is shown in FIGS. 13-14. In particular, needle portion (1100) comprises an integrated distal tissue piercing tip (1102) and a hollow cutter passage (1106). A cutter (1130) is slidably disposed in hollow cutter passage (1106). Integrated piercing tip (1102) of the present example is formed by flattening the distal end of needle portion (1100), then grinding away the top layer of the flattened material (leaving only one wall thickness of material), and then grinding the remaining flattened material to form a blade (this blade may take on various shapes). Rotatable needle portion (1100) of this example rotatably attaches to body (4), and is rotatable about its longitudinal axis, relative to body (4). Hollow cutter (1130) is shown slidably and rotatably mounted in hollow cutter passage (1106), with a distal cutting end (1132) adjacent to integrated distal tissue piercing tip (1102). Vacuum is applied through the cutter (1130) in order to prolapse tissue into the receiving aperture (1105). A gap between the outer diameter of cutter (1130) and inner diameter of needle (1100) extends longitudinally in parallel with hollow cutter passage (1106), and communicates venting to cutter (1130) in order to create a pressure differential to transport tissue samples proximally through cutter (1130). It should be understood, however, that these features of needle portion (1100) are merely exemplary, and that needle portion (1100) may be modified in any suitable fashion.

II. Exemplary Cutter

As further shown, a hollow cutter (50) is disposed within cannula lumen (20). Cutter (50) of this example has a generally half-cylindrical configuration near its distal end, with a generally tubular configuration for the remainder of its length. In particular, and as shown in FIGS. 4A-6B, a distal portion of cutter (50) has a sharp longitudinal edge (51) and a flat longitudinal edge (53). Edges (51, 53) define a gap (54) therebetween, and proximally terminate at a rear edge (55). In the present example, the distal ends of edges (51, 53) define a circumferential perimeter extending through an angular range of approximately 190° (e.g., a little more than 190°, etc.) about a central axis defined by cutter (50). The proximal ends of edges (51, 53) define a circumferential perimeter extending through an angular range of approximately 180° (e.g., a little more than 180°, etc.) about a central axis defined by cutter (50). Alternatively, any other angle or angular range may be used to define the circumferential perimeter at any longitudinal position along gap (54). In the present example, flat longitudinal edge (53) extends substantially parallel to the longitudinal axis defined by cutter (50); while sharp longitudinal edge (51) is inclined at approximately 4° relative to the longitudinal axis defined by cutter (50). Of course, sharp longitudinal edge (51) may have any other desired incline, to the extent that sharp longitudinal edge (51) has any incline.

With cutter (50) of the present example disposed in cannula (12), rear edge (55) is at a longitudinal position just proximal to the proximal edge of transverse aperture (16). The interior of cutter (50) defines a cutter lumen (52), such that fluid and tissue may be communicated through cutter (50) via cutter lumen (52). As will be described in greater detail below, cutter (50) is configured to rotate within cannula lumen (20). In particular, cutter (50) is configured to sever a biopsy sample from tissue protruding through transverse aperture (16) of cannula (12). Such severing is accomplished through shearing cooperation between sharp longitudinal edge (51) of cutter (50) and shearing edge (17) of cannula (12). In particular, cutting occurs because of shearing at both edges (17) of cannula (12) and rotation of cutter cutting edge (51) by more than 190° within cannula (12).

FIGS. 4A-6B depict a series where cutter (50) is rotated from an open position to a closed position. In particular, FIGS. 4A-4B depict cutter (50) in an open position where gap (54) of cutter (50) is positioned to correspond with aperture (16) of cannula (12), such that gap (54) substantially aligns with aperture (16). As will be described in more detail below, a portion of tissue may be drawn into aperture (16) and thus also gap (54) of cutter (50), under influence of a vacuum drawn through cutter lumen (52), while cutter (50) is in an open position. When cutter (50) is in this position, cutter (50) closes off opening (32), thus closing off fluid communication between cannula lumen (20) and vent lumen (40). Cutter lumen (52) is therefore not vented in the present example when cutter (50) is in the open position. Cutter (50) and/or cannula (12) may include a protrusion or some other feature to assist in sealing of opening (32), or to otherwise prevent venting of cutter lumen (52), when cutter (50) is in an open position as shown in FIGS. 4A-4B. Alternatively, a two-way valve in communication with opening (42), as described above, may be used to prevent venting of cutter lumen (52), when cutter (50) is in an open position as shown in FIGS. 4A-4B.

As cutter (50) rotates to a partially-closed position as shown in FIGS. 5A-5B, sharp longitudinal edge (51) and shearing edge (17) begin to cooperatingly sever the tissue that is drawn into aperture (16). As shown in this example, cutter (52) rotates in a manner such that gap (54) rotates towards a position proximate to wall (30). As cutter (50) rotates to a partially-closed position, cutter (50) also starts to open opening (32), thus permitting venting of cannula lumen (20) and cutter lumen (52). With a vacuum being drawn through the proximal end of cutter lumen (52) as will be described in greater detail below, such venting may create a pressure differential urging severed tissue proximally through cutter lumen (52).

FIGS. 6A-6B depict cutter (50) in a closed position. In a closed position, gap (54) of cutter (50) is positioned proximate to wall (30). With sharp longitudinal edge (51) having surpassed shearing edge (17) at this position, sharp longitudinal edge (51) and shearing edge (17) will have completely severed a tissue sample through a shearing action. Furthermore, with cutter (50) in a closed position, cutter (50) fully opens opening (32), thus permitting venting of cannula lumen (20) and cutter lumen (52), while closing off aperture (16). With a vacuum being drawn through the proximal end of cutter lumen (52) as will be described in greater detail below, such venting may create a pressure differential drawing the severed tissue sample proximally through cutter lumen (52).

Cutter (50) may be rotated over any suitable angular range. For example, cutter (50) may be rotated 180 degrees or 190 degrees when rotating from an open to closed position, and vice versa. Alternatively, any other suitable angular range for cutter (50) rotation may be used. An exemplary mechanism for rotating cutter (50) will be described in greater detail below, while other suitable mechanisms will be apparent to those of ordinary skill in the art in view of the teachings herein. Furthermore, while cutter (50) only rotates in the present example, without also translating longitudinally, it should be understood that other versions of biopsy device (2) may have a cutter (50) that just translates longitudinally without rotating, a cutter (50) that rotates in addition to translating longitudinally, a cutter that reciprocates rotationally and/or translationally, or a cutter (50) that performs any other suitable type of movement.

Figure 7:
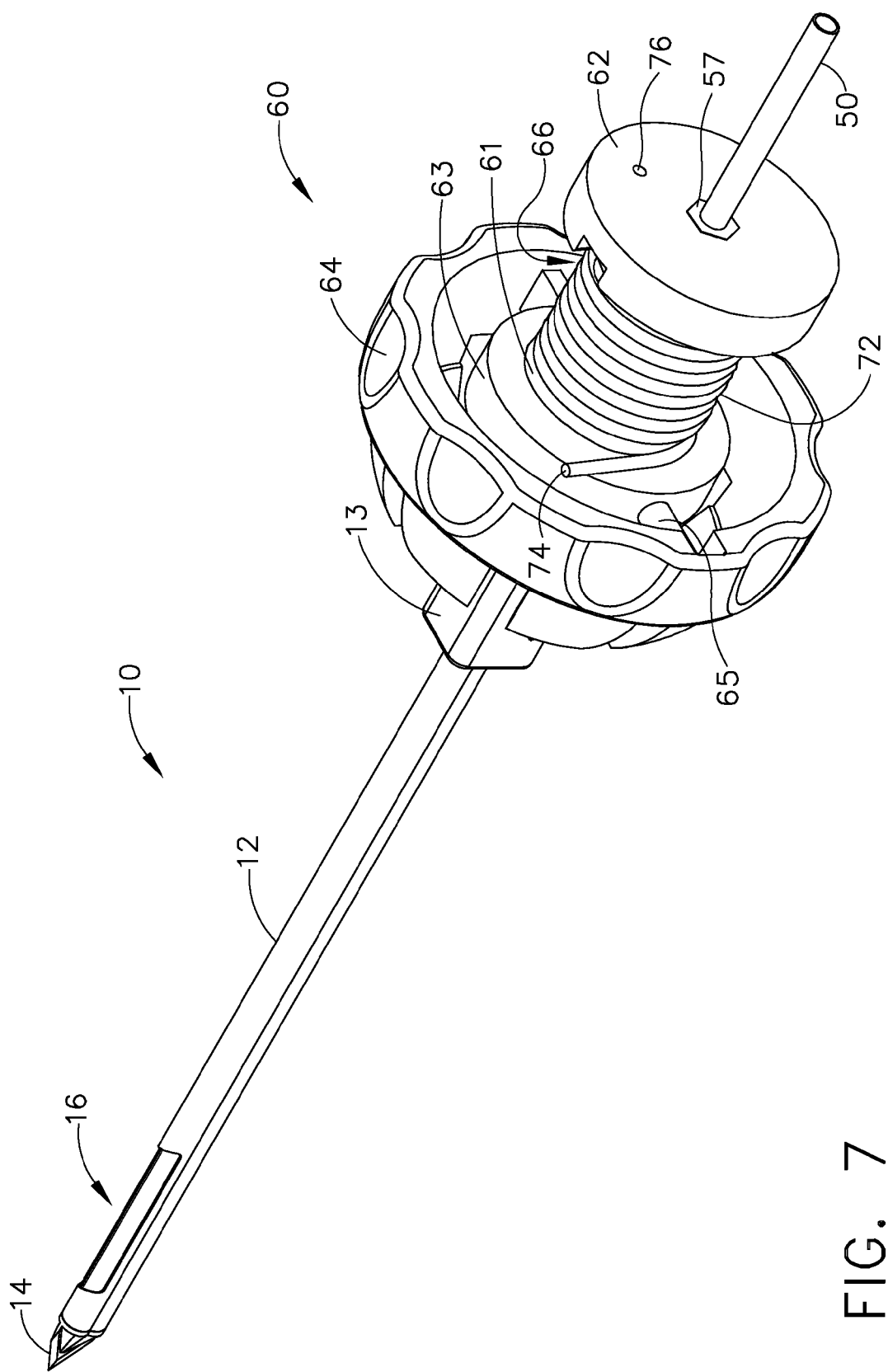
FIG. 7 is a perspective view of components of the cutter firing mechanism of the biopsy device of FIG. 1.

As shown in FIG. 7, cutter (50) also has a hexagonal overmold (57) formed near its distal end. For instance, cutter (50) may be formed of a metal material while overmold (57) may be formed of a plastic molded over a portion of cutter (50). Of course, any other suitable material or combination of materials may be used for any of these components. Overmold (57) of the present example is configured to rotate unitarily with cutter (50). As will be described in greater detail below, overmold (57) is configured to engage with a cutter loader (60), which is operable to rotate cutter (50) in an actuation stroke.

As will also be described in greater detail below, cutter (50) is further configured to permit severed tissue samples to be communicated proximally through cutter lumen (52). Other illustrative examples of such severing and proximal communication are described in U.S. Pat. No. 5,526,822, entitled "Method and Apparatus for Automated Biopsy and Collection of Soft Tissue," granted Jun. 18, 1996, the disclosure of which is incorporated by reference herein, though any other suitable structures or techniques may be used for severing and/or communicating tissue samples within a biopsy system (2).

Cutter (50) may be subject to various treatments or configurations in order to facilitate proximal communication of tissue samples through cutter lumen (52). Examples of various treatments and configurations are disclosed in U.S. Pub. No. 2008/0214955, entitled "Presentation of Biopsy Sample by Biopsy Device," published Sep. 4, 2008, the disclosure of which is incorporated by reference herein. Still other suitable variations of cutter (50) will be apparent to those of ordinary skill in the art in view of the teachings herein.

III. Exemplary Cutter Actuation Mechanism

Figure 8:
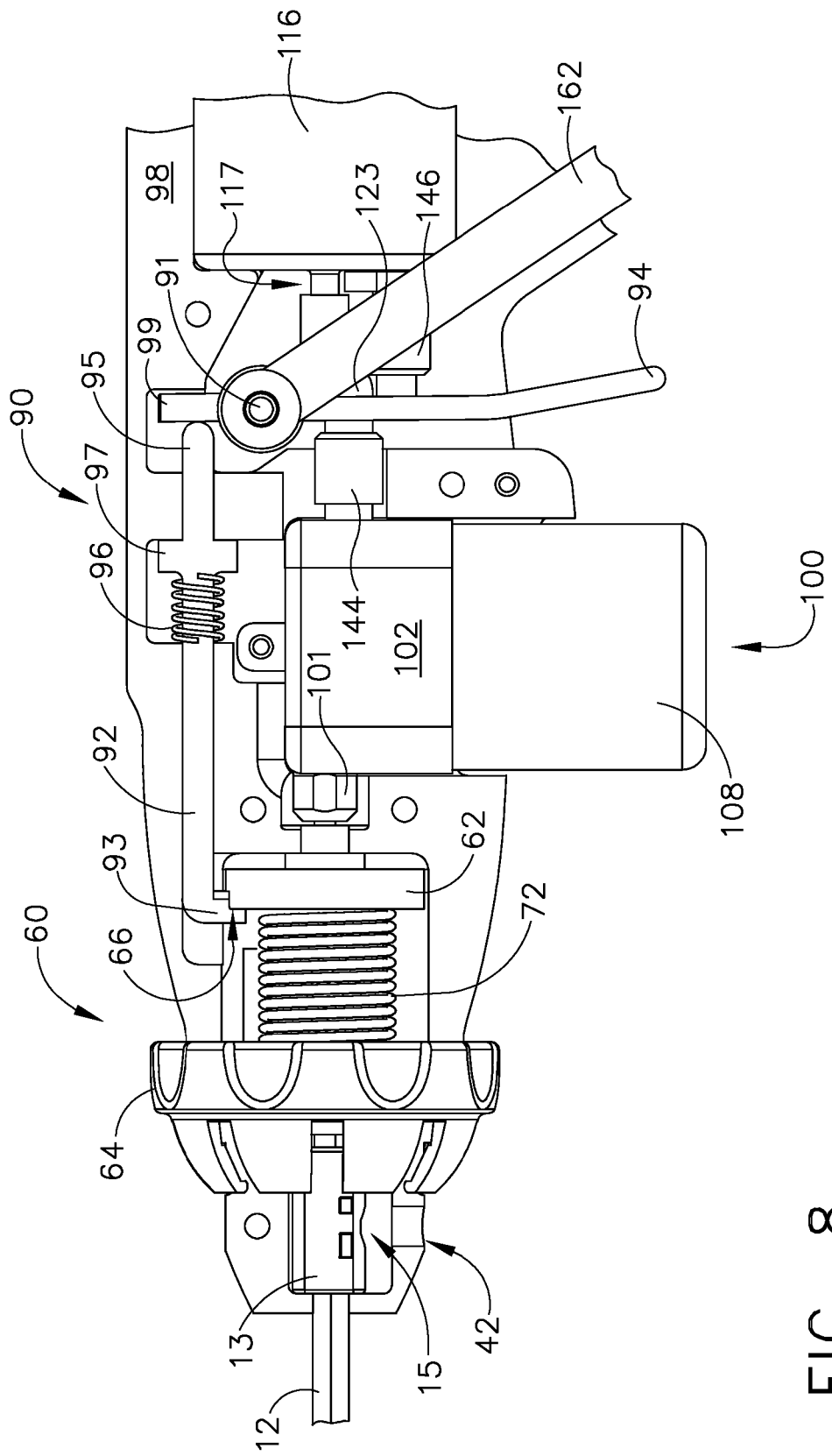
FIG. 8 is a partial, side cross-sectional view of the cutter firing mechanism of the biopsy device of FIG. 1, in a cocked configuration.
Figure 9:
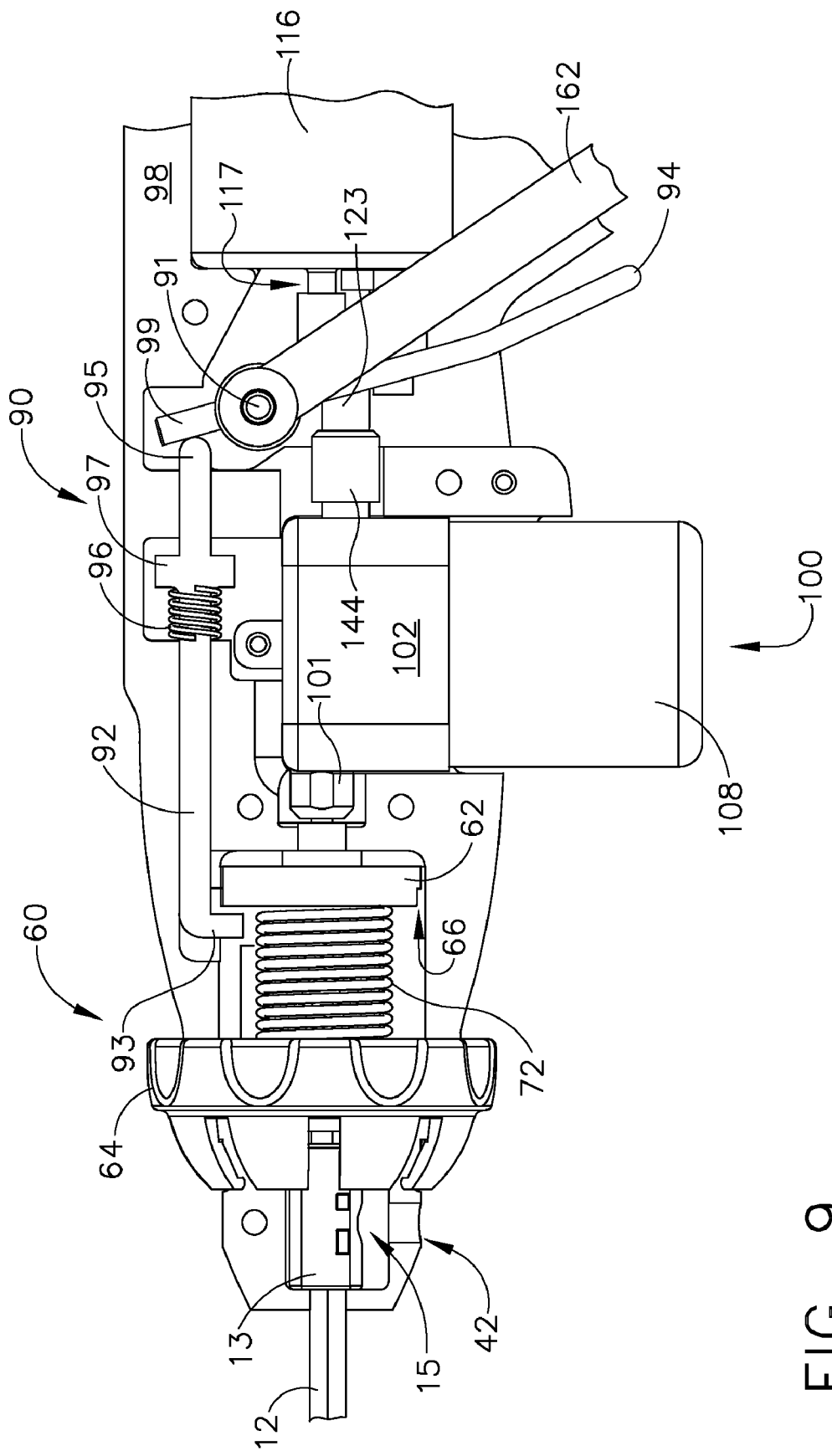
FIG. 9 is a partial, side cross-sectional view of the cutter firing mechanism of the biopsy device of FIG. 1, in a fired configuration.

An exemplary cutter loader (60) is shown in FIGS. 7-9. Cutter loader (60) is operable to store and communicate the energy to rotate cutter (50). In this example, the act of loading cutter (50) includes rotating cutter (50) into an open position. Cutter loader (60) is configured to hold cutter (50) in the open position and store the energy that will be used to rotate cutter (50). Cutter loader (60) may then be actuated to communicate energy to rotate cutter (50) to the closed position to sever a tissue sample. Body (4) is configured to support cutter loader (60) via a plurality of bearings. The bearings are configured to allow at least some rotation of cutter loader (60) relative to body (4). The angular range for rotation of cutter loader (60) may vary. For example, cutter loader (60) may rotate along the same angular range as cutter (50) (e.g., between 180 to 190 degrees, etc.) and/or along any other suitable angular range.

Cutter loader (60) of the present example comprises a spool body (61) having a proximal flange (62) and a distal flange (63). By way of example only, distal flange (63) may be secured to spool body (61) while proximal flange (63) is formed unitarily with spool body (61). Alternatively, any other suitable configurations or relationships may be used. In the present example, a torsion spring (72) is disposed about a central region of spool body (61) as will be described in greater detail below. A notch (66) is formed in proximal flange (62), as will also be described in greater detail below. A pin (65) extends transversely from distal flange (63), and is engaged with a knob (64). In particular, engagement between knob (64) and pin (65) is such that rotation of knob (64) effects rotation of spool body (61). Knob (64) is rotatable relative to body (4), such that an operator may rotate knob (64) to load cutter loader (60). Spool body (61) also defines a hexagonal bore, through which overmold (57) of cutter (50) is inserted. Thus, engagement between spool body (61) and overmold (57) is such that rotation of spool body (61) effects rotation of cutter (50), as will be described in greater detail below.

As noted above, cutter loader (60) includes a spring (72) having a distal end (74) and a proximal end (76). Distal end (74) of spring (72) is coupled to a portion of body (4) or another stationary member. Proximal end (76) of spring (72) is insertingly coupled to proximal flange (62) of cutter loader (60).

Spring (72) has a relaxed state when cutter loader (60) is at a first rotational position (e.g., when cutter (50) is in a closed position). Spring (72) has an activated state when cutter loader (60) is at a second rotational position (e.g., when cutter (50) is in an open position). In particular, spring (72) is in an activated state when spring (72) is twisted by manual rotation of knob (64) and locked in place. Spring (72) is biased to urge cutter (50) to a closed position.

Cutter loader (60) is operable to rotate proximal end (76) of spring (72) relative to distal end (74) of spring (72) and thus position spring (72) in an activated state. More particularly, cutter loader (60) is configured to position spring (72) in an activated state when loading cutter (50) such that cutter (50) may be later operated to sever a tissue sample by using the energy released from the activated spring (72) while returning to a relaxed state.

As also noted above, proximal flange (62) of cutter loader (60) includes a notch (66) that is configured to engage a portion of a trigger mechanism (90). This engagement between notch (66) and trigger mechanism (90) locks cutter (50) in an open position, resisting the rotational urging of spring (72). In particular, and as shown in FIGS. 8-9, trigger mechanism (90) of the present example comprises an arm (92) having a tab (93) on its distal end that is configured to engage with notch (66). Tab (93) may have any suitable shape and size. For example, tab (93) may have a rectangular shape. Tab (93) may also have one or more chamfered corners to facilitate engagement and/or disengagement with notch (66), particularly when arm (92) and spool body (61) are each under a spring bias.

Arm (92) also has a proximal tip (95) and a boss (97) located between tab (93) and proximal tip (95). A spring (96) is positioned about arm (92), and is engaged between housing (98) of body (4) and boss (97). Spring (96) is biased to urge arm (92) proximally; while boss (97) is configured to engage housing (98) to restrict proximal movement of arm (92). As arm (92) is being advanced in a distal direction through housing (98), spring (96) is compressed against housing (98). Housing (98) thus provides sufficient clearance to permit some longitudinal movement of arm (92) and spring (96).

Trigger mechanism (90) of the present example further comprises a pivoting lever (94). As shown in FIGS. 1-2 and 8-12, lever (94) protrudes from housing (98) sufficiently to permit a user to actuate lever (94) with a the same hand that is gripping biopsy device (2). For instance, a user may actuate lever (94) with a single finger. As shown in FIGS. 8-9, lever (94) is configured to pivot about a pivot pin (91), which is secured relative to housing (98). Lever (94) includes a firing arm (99), which is configured to engage proximal tip (95) of arm (92). Lever (94) is operable to supply the force necessary to advance arm (92) in a distal direction. In particular, lever (94) is pivotable such that a force exerted on the exposed portion of lever causes firing arm (99) to rotate in the same direction. Thus, as illustrated in the series represented by FIGS. 8-9, and lever (94) is operable to force the movement of arm (92) in a distal direction to disengage notch (66).

Upon sufficient disengagement of tab (93) from notch (66), spool body (61) rotates under urging of spring (72), thereby rotating cutter (50) from the open position to the closed position. Such rotation of spool body (61) will rotationally move notch (66) away from tab (93). With arm (92) being proximally biased by spring (96), tab (93) may rest on the distal face of proximal flange (62) until spool body (61) is again rotated to bring notch (66) back to tab (93). As noted above, such rotation may be effected by a user gripping and rotating knob (64). Upon sufficient rotation of spool body (61), against the urging of spring (72), to bring notch (66) back to tab (93), the proximal bias of spring (96) may ultimately pull tab (93) back into notch (66). Firing mechanism (90) will then again be in a cocked configuration, ready for the next firing stroke.

As described above, the disengagement of tab (93) from notch (66) allows spring (72) to retract to its original position. Referring to FIG. 7, proximal end (76) of spring (72) will rotate with proximal flange (62) in a counterclockwise direction. With cutter (50) being unitarily secured relative to cutter spool (61) (via overmold (57)), cutter (50) will also rotate in a counterclockwise direction when tab (93) is disengaged from notch (66) by actuation of lever (94). More specifically, movement of spring (72) from an loaded position to an unloaded position results in the rotation of cutter (50) from a loaded position (e.g., open position) as shown in FIG. 4A to a closed position as shown in FIG. 6A. During the movement of cutter (50) from this first position to this second position, cutter (50) severs a tissue sample located in gap (54) of cutter (50). The tissue sample may then be pulled through cutter lumen (52) to a tissue collection chamber (100) under the influence of a vacuum system (110) as described in greater detail below. Distal end (74) of spring (72) stays substantially stationary during this process of cutter actuation.

An exemplary use of cutter loader (60) will now be described. First, needle portion (10) is inserted into a patient's breast with cutter (50) in a closed position (e.g., closing off aperture (16)). Then, referring to the view provided by FIG. 7 (looking from the proximal to distal direction), knob (64) of cutter loader (60) is rotated in a clockwise direction. Rotating knob (64) in this direction causes the respective rotation of cutter (50), proximal flange (62) of cutter loader (60), and proximal end (76) of spring (72) as shown in FIG. 8. Rotation of cutter (50) in this manner will result in cutter (50) rotating to an open position and thus exposing gap (54) to receive at least a portion of tissue as shown in FIGS. 4A and 4B. Rotation of knob (64) positions spring (72) in a loaded state by rotating proximal end (76) of spring (72). It will be understood that rotation of proximal end (76) of spring (72) may constitute activating spring (72). In order to finish loading cutter (50), the positioning of spring (72) in an activated state should be locked in this example. As explained earlier, trigger (90) is responsible for maintaining spring (72) in an activated state by engaging notch (66), which is located at the 12 o'clock position to engage tab (93), as shown in FIG. 8. Spring (96) provides sufficient proximal bias to arm (92) to pull tab (93) into notch (66) when notch (66) reaches the 12 o'clock position. Cutter (50) is in a closed position when spring (72) is a relaxed state; and an open position when spring (72) is in an activated state, as held by engagement of tab (93) with notch (66).

The engagement of notch (66) with tab (93) of trigger (90) retains spring (72) in an activated state until trigger (90) is operated to terminate its engagement with notch (66) and thus allow spring (72) to return to a relaxed state as shown in FIG. 9. As spring (72) returns to a relaxed state, proximal end (76) of spring (72) rotates in a counterclockwise direction (looking from the proximal to distal direction) and forces cutter loader (60) to rotate in the same direction. The rotation of cutter loader (60) results in the rotation of cutter (50) from an open position to a closed position. This rotation of cutter (50) severs a tissue sample.

Of course, cutter loader (60) may take a variety of forms, and is certainly not limited to the precise configuration described herein. For instance, cutter loader (60) may have any other suitable features, components, or configurations. Similarly, cutter loader (60) may be operated in a variety of other ways. For instance, directions of rotation may be reversed (e.g., rotate knob (64) counterclockwise to load spring (72), etc.). Other suitable features, components, configurations, and methods of operation for cutter loader (60) will be apparent to those of ordinary skill in the art in view of the teachings herein.

IV. Exemplary Tissue Collection Chamber

Figure 12:
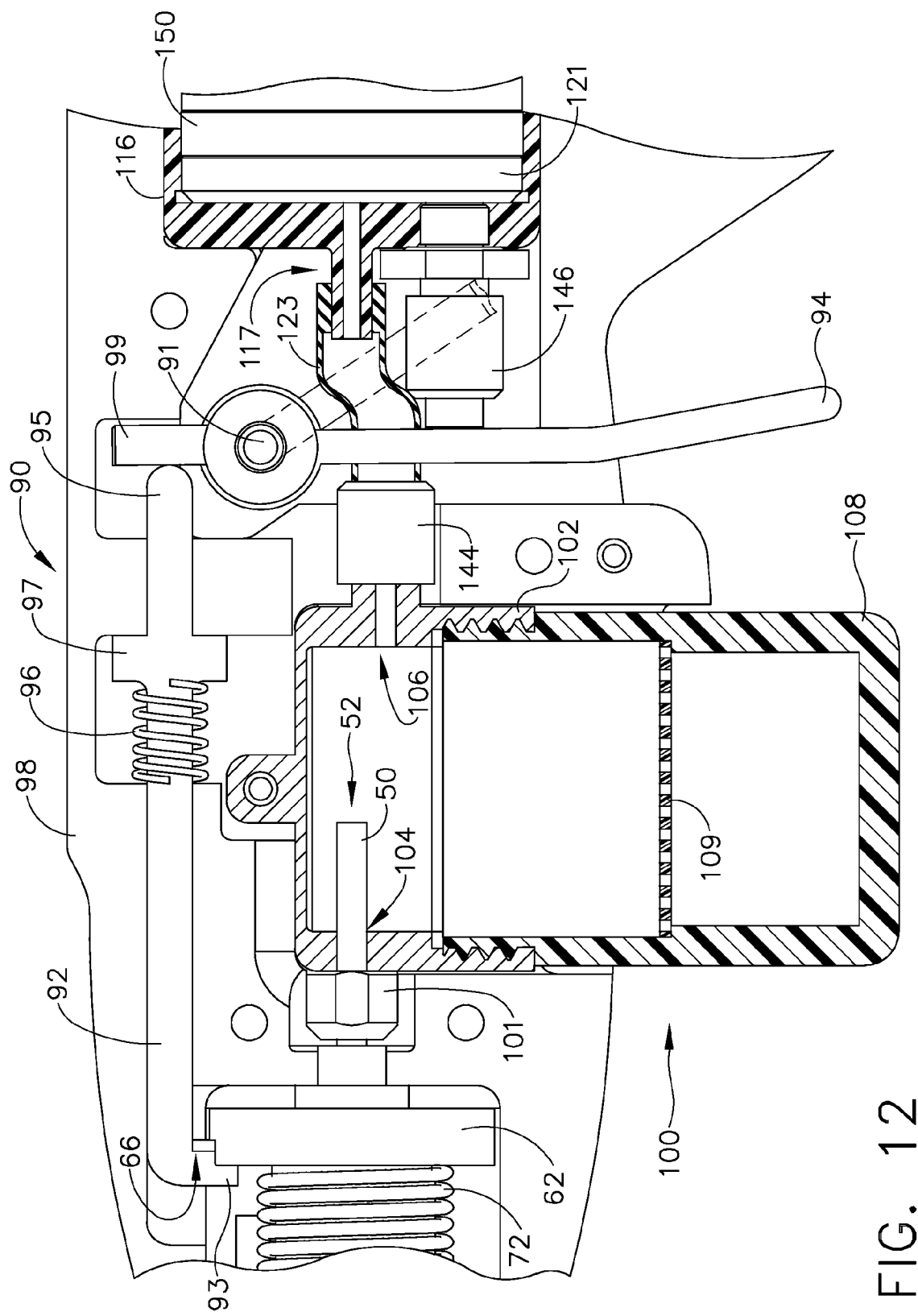
FIG. 12 is a partial, side cross-sectional view of the vacuum chamber and tissue collection chamber of the biopsy device of FIG. 1.

As shown in FIG. 12, tissue collection chamber (100) of the present example comprises a cup (108) and a base (102) having a plurality of ports (104, 106). In this example, base (102) is component that is formed separately from body (4) yet coupled with body (4). However, in some versions, base (102) is a unitary component of body (4). Port (104) is positioned on the distal side of base (102), and receives the proximal end of cutter (50). In particular, the proximal end of cutter (50) is inserted through port (104), and terminates within the interior of tissue collection chamber (100). The interior of tissue collection chamber (100) is thus in fluid communication with cutter lumen (52). This fluid communication enables tissue collection chamber (100) to receive tissue samples communicated proximally through cutter lumen (52) as will be described in greater detail below. A seal (101) maintains a fluid seal at the interface of cutter (50) and port (104), even as cutter (50) rotates during actuation of cutter (50). Port (106) is positioned opposite port (104), on the proximal side of tissue collection chamber (100), and is in fluid communication with vacuum system (110).

Base (102) removably supports cup (108), such that cup (108) is configured to unscrewed from base (102). Cup (108) is positioned below port (104), such that tissue samples communicated proximally through cutter lumen (52) may be deposited into cup (108). In this example, cup (108) includes a screen (109) capable of supporting a tissue sample while permitting fluids to pass therethrough. Similarly, screen (109) may include various ribbing, apertures, voids, projections, or utilize any other suitable structure or technique that allows a tissue sample to be received by screen (109). Cup (108) may receive the entirety of a tissue sample such that no portion of the tissue sample projects from cup (108).

Likewise, cup (108) may be configured to receive a plurality of tissue samples. Cup (108) may also be configured such that it is reusable. Each cup (108) may respectively comprise one or more types of markings or other indicia to distinguish one cup (108) from another cup (108). Examples of markings or other indicia to distinguish one cup (108) from another cup (108) are disclosed in U.S. Pub. No. 2008/0214955, entitled "Presentation of Biopsy Sample by Biopsy Device," published Sep. 4, 2008, the disclosure of which is incorporated by reference herein.

While cup (108) is screwed onto base (102) in the present example, it should be understood that cup (108) may engage with base (102) in any other suitable fashion. By way of example only, cup (108) may be forcibly engaged with base (102) by being slidably engaged within a portion of base (102), cup (108) and base (102) may provide bayonet mounting structures, a snap fit, etc. It should also be understood that collection chamber (100) may have any suitable shape or size. For example and as shown in FIG. 12, tissue collection chamber (100) has a generally cylindrical shape when base (102) and cup (108) are engaged. Further, the shape and size of base (102) and cup (108) may be configured to optimally allow the combination to receive a severed tissue sample. Further the respective inner surfaces of base (102) and cup (108) may include various ribbing, apertures, voids, projections, surface treatments, or utilize any other suitable structure or technique that allows a tissue sample to be received by collection chamber (100).

Those of ordinary skill in the art will appreciate that tissue collection chamber (100) may take a variety of alternative forms. For instance, tissue collection chamber (100) may provide a plurality of discrete tissue sample chambers that may be successively indexed to cutter lumen (52). Other suitable features, components, configurations, and methods of operation for a tissue collection chamber (100) will be apparent to those of ordinary skill in the art in view of the teachings herein.

V. Exemplary Vacuum System

Figure 10:
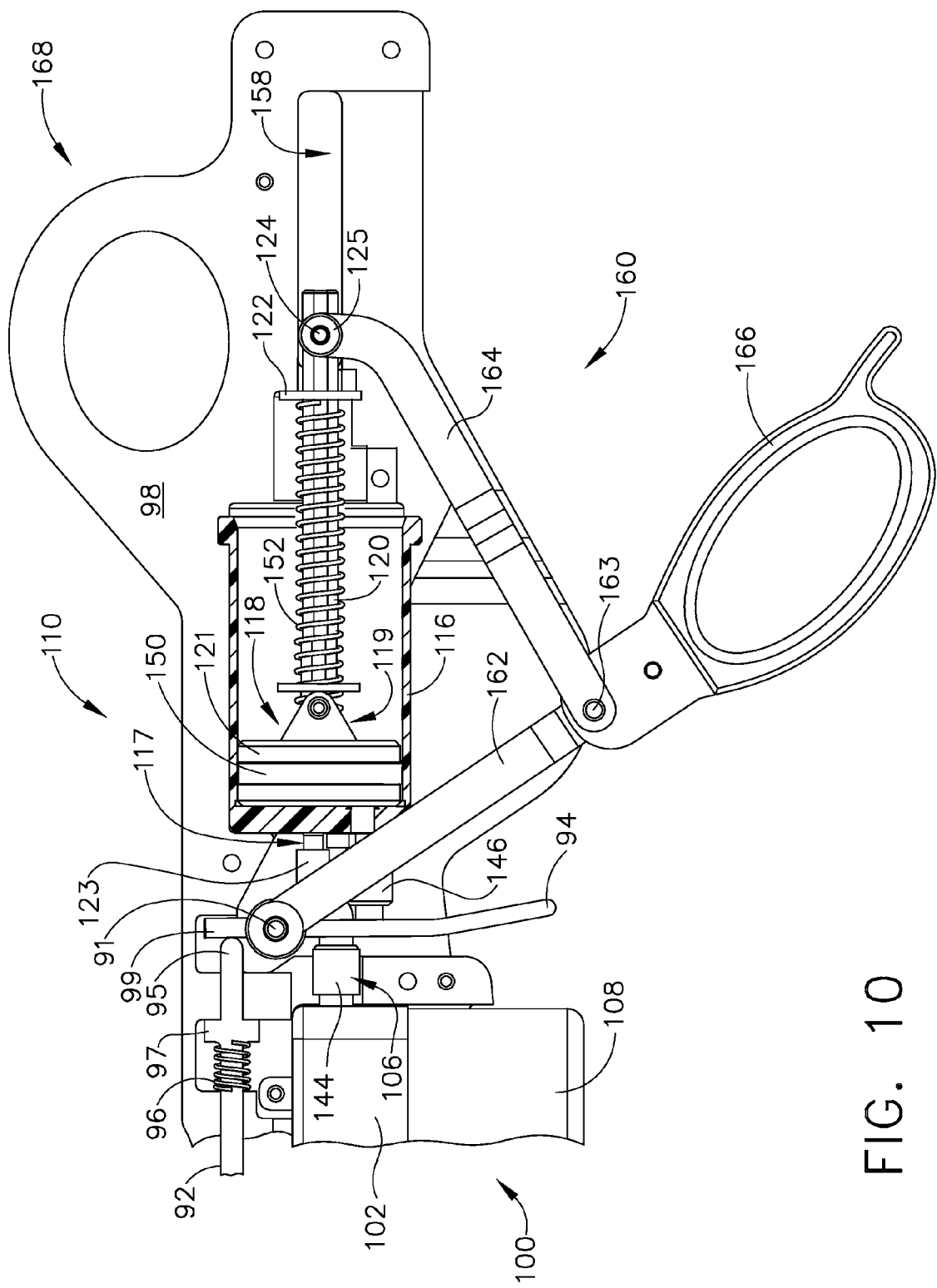
FIG. 10 is a partial, side cross-sectional view of the vacuum pump assembly of the biopsy device of FIG. 1, with the pump handle in an unactuated position.
Figure 11:
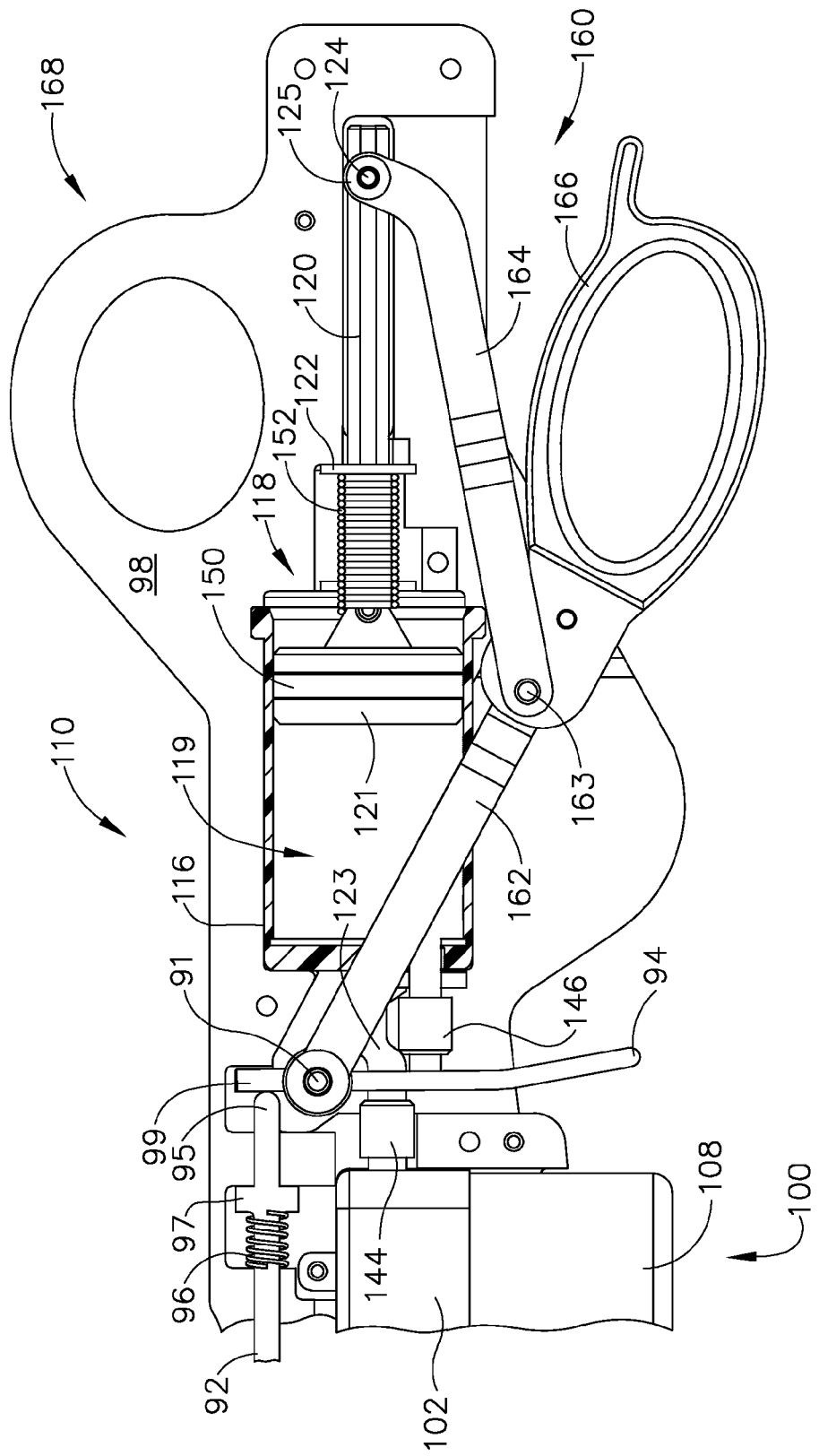
FIG. 11 is a partial, side cross-sectional view of the vacuum pump assembly of the biopsy device of FIG. 1, with the pump handle in an actuated position.

As noted above, a tissue sample is drawn into tissue collection chamber (100) by a vacuum induced within tissue collection chamber (100) by vacuum system (110). As shown in FIGS. 10-11, vacuum system (110) is located in handle portion (160) of body (4), and comprises a pump and a pair of lever arms (162, 164) that are operable to drive the pump. More particularly, the pump comprises a cylinder (116) oriented along a longitudinal axis running from the proximal end of biopsy device (2) to the distal end of biopsy device (2). Cylinder (116) defines a bore (119).

A piston (118) is partly located within bore (119) of pump cylinder (116). Piston (118) includes a piston rod (120) that projects rearwardly from a head (121). Head (121) of piston (118) has a disc-like shape and at least one groove (not shown) defining by an annular space. A sealing member (150), such as an O-ring, is positioned in the groove and has a size operable to create a seal between head (121) and the inner surface of bore (119). Head (121) is thus sealingly engaged with the surface of bore (119) in cylinder (116), while head (121) is configured to move longitudinally within cylinder (116) from a proximal position (FIG. 11) to a distal position (FIG. 10).

A spring (152) is disposed about rod (120). The distal end of spring (152) is engaged with head (121), while the proximal end of spring (152) is engaged with a washer (122). Washer (122) is engaged with housing (98) of body (4), such that washer (122) remains stationary, providing a base for spring (152). Spring (152) is biased to urge head (121) distally, to the position shown in FIG. 10.

As shown in FIG. 12, the distal end of cylinder (116) includes a port (117) that is in fluid communication with port (106) via a conduit (123). A vacuum induced within cylinder (116) may thus be communicated to tissue collection chamber (100). With tissue collection chamber (100) being in fluid communication with cutter lumen (52), the vacuum may also thus be induced within cutter lumen (52). A one-way check valve (144) is provided at the interface of conduit (123) and port (106), and is configured to only permit air to be communicated proximally from tissue collection chamber (100) to cylinder (116). In other words, check valve (144) prevents air from being communicated from cylinder (116) to tissue collection chamber (100).

A one-way check valve (146) is also provided at the distal end of cylinder (116). Check valve (146) is configured to permit air to be communicated from cylinder (116) through check valve (146) (e.g., to atmosphere); while preventing air from being communicated to cylinder (116) through check valve (146). Accordingly, proximal longitudinal linear motion of head (121) may induce a vacuum within cylinder (116) (and, hence, within tissue collection chamber (100) and cutter lumen (52)); while distal longitudinal motion of head (121) may permit evacuation of air from cylinder (116). At least some of such evacuated air may be introduced to cylinder (116) through the venting process described above with reference to openings (32, 42) as cutter (50) reaches a closed position. Of course, as noted above, opening (42) may have a two-way valve as described above, or any other valve, if desired, such as to avoid vacuum leaking, etc.

Handle (160) is operable to actuate vacuum system (110) by translating rod (120) and head (121) longitudinally. In particular, handle (160) comprises a finger grip member (166), a thumb grip portion (168) of housing (98), a first lever arm (162), and a second lever arm (164). A distal end of first lever arm (162) is pivotally engaged with pivot pin (91), which is incidentally the same pivot pin (91) that lever (94) of trigger mechanism (90) is pivotally engaged with. First lever arm (162) is thus operable to pivot relative to housing (98) about pivot pin (91). The proximal end of first lever arm (162) is fixedly secured to finger grip member (166). Another pivot pin (163) is provided near the interface of first lever arm (162) and finger grip member (166). Second lever arm (164) is pivotally engaged with pivot pin (163). First lever arm (162) and second lever arm (164) are thus operable to pivot relative to each other about pivot pin (163).

Second lever arm (164) is also pivotally engaged with rod (120) by a pivot pin (124). A roller bearing (125) is provided about pivot pin (124), and is configured to support the proximal end of rod (120). Housing (98) defines a track (158) that is configured to receive roller bearing (125). In particular, track (158) permits roller bearing (125) to translate (i.e., reciprocate) within housing (98), such as during actuation of vacuum system (110).

In this example, a stroke of grip member (166) effects a stroke of piston (118) and requires exerting a force on grip member (166) that rotates first arm (162) in a counterclockwise direction about pin (91) toward the proximal end of body (4). Exerting this force on arm (162) causes the upper end of second arm (164) to be axially driven in a proximal direction with rod (120). Driving rod (120) in this proximal direction also drives head (121) in a proximal direction. As head (121) travels in a proximal direction, head (121) in combination with sealing member (150) forces the air that is in bore (119) to travel out of bore (119) via the proximal end of pump cylinder (116). Retracting head (121) in this proximal direction towards washer (122) compresses spring (152). As shown in FIG. 11, rod (120) is moved in a proximal direction until head (121) substantially reaches the proximal end of bore (119).

After piston (118) is moved axially in a proximal direction and head (121) has finished drawing a vacuum, piston (118) is urged back to its relaxed position via spring (152) as spring (152) travels from a compressed position back to a relaxed or otherwise extended position. As head (121) travels in a distal direction with spring (152), a check valve (144) at port (106) prevents the air in bore (119) from traveling in a distal direction back into tissue collection chamber (100). Instead, air is driven out of bore (119) via check valve (146) as head (121) travels in a distal direction. Several strokes may be used to operate vacuum source (110), such that more than one stroke of grip member (166) may be effectuated consecutively to respectively allow air to enter bore (119) as piston (118) travels in a proximal direction. Using piston (108) to remove air from bore (119) and allow air from port (106) to flow into bore (119) produces a vacuum effect. In this example, the vacuum force produced by a stroke of vacuum source (110) equals a value in the range of 18-20 in. Hg. Of course, any other suitable level of vacuum may be provided.

In the present example, the vacuum induced by vacuum system (110) travels through port (117), conduit (123), port (106), tissue collection chamber (100), and cutter lumen (52). The vacuum may be used in a variety of ways. For example, a vacuum may be used to draw a portion of tissue into aperture (16) of cannula (12), and gap (54) of cutter (50), such that the tissue may later be severed by cutter (50). The vacuum induced by vacuum system (110) may also be used to draw a severed tissue sample through cutter lumen (52) and into tissue collection chamber (100). For example, after a tissue sample has been severed, at least one stroke may be applied to grip member (166) and thus cause a vacuum force to be directed through cutter lumen (52). As mentioned earlier, successive strokes may be performed to increase the vacuum force applied. Alternatively, an initial actuation of vacuum system (110) may suffice to both draw tissue into aperture (16) of cannula (12) and gap (54) of cutter (50) as well as drawing the severed tissue sample proximally through cutter lumen to reach tissue collection chamber (100).

Of course, cutter (50) may be loaded, and triggered to sever another tissue sample after a first tissue sample is obtained. Once again, a vacuum force from vacuum system (110) may be created to transfer this second tissue sample into tissue collection chamber (100) with the first tissue sample.

As shown in FIGS. 10-11, and as described above, exerting a squeezing force on finger grip member (166) (e.g., toward body (4)) causes piston (118) to translate proximally away from port (117), to a proximal position, due in part to the dual pivoting action of lever arms (162, 164). Such a force may be exerted on finger grip member (166) by a user using a single hand. For instance, the user may grip device (2) with one hand, where at least one of the user's fingers engages finger grip member (166) and the user's thumb engages thumb grip portion (168). The user may then squeeze with that hand to urge finger grip member (166) toward body (4). It will also be appreciated that, even with the user's hand being used in such a way, the user's index finger (and/or one or more other fingers) may still be free to pull lever (94) of trigger mechanism (90) to actuate cutter (50). In other words, a user may both actuate vacuum system (110) and trigger mechanism (90) with the same single hand, without having to reposition any part of the user's hand between acts of actuating vacuum system (110) and actuating trigger mechanism (90).

As the user releases his or her grip on finger grip member (166) and/or thumb grip portion (168), the bias of spring (152) may urge piston (118) to translate distally toward port (117), to a distal position. This same resilient urging, and resulting distal movement of piston (118), may also urge finger grip member (166) away from body (4). Creating a vacuum in tissue collection chamber (100) and cutter (50) may thus be achieved by operating vacuum system (110) and generally exerting a plurality of strokes of grip member (166) in the above described manner whereby piston (118) is retracted proximally and then advanced distally back to its original position.

As with any other components described herein, vacuum system (110) may be modified in any way desired. Alternatively, vacuum system (110) may be omitted altogether. For instance, an external source of vacuum may be coupled with biopsy device (2). In other versions, biopsy device (2) operates with no vacuum at all. Furthermore, vacuum system (110) may be operated in any other suitable fashion. Other suitable components, features, configurations, and methods of operation for vacuum system (110) will be apparent to those of ordinary skill in the art in view of the teachings herein.

VI. Exemplary Use of Biopsy Device

In an exemplary use of biopsy device (2), a user squeezes finger grip member (166) toward body (4) one or more times (e.g., three times) to induce a vacuum as described above, while cutter (50) is in a closed position. The user then inserts needle portion (10) into a patient's breast while cutter (50) is in the closed position. The user then rotates knob (64) to cock firing mechanism (90). In particular, the user rotates knob (64) until tab (93) engages notch (66) under the resilient urging of spring (96). Such engagement may be indicated to the user in a tactile or audible fashion. With firing mechanism (90) cocked, the cutter (50) is moved to an open position, and vacuum created by vacuum system (110) draws tissue into aperture (16). The user may then pull trigger (94) to fire cutter (50). Such firing of cutter (50) may sever the tissue sample and provide the venting through openings (32, 42) described above. To the extent that opening (42) has a valve as described above, the user may open the valve and close the valve between each cutting stroke to move between venting at the closed position (e.g., for tissue transportation) and the closed position (e.g., to generate vacuum). Due to the combination of such venting and the vacuum created by vacuum system (110), the severed tissue sample may be drawn proximally through cutter lumen (52) and deposited on screen (109) in tissue collection chamber (100). The above steps may be repeated (from the beginning of the above process or starting at any of the above steps) until a desired number of tissue samples are obtained.

After the user has withdrawn needle portion (10) from the patient's breast, the user may unscrew cup (108) from base (102) to inspect one or more tissue samples that are on screen (109).

In the above example, the user actuates vacuum system (110) before inserting needle portion (10) into the patient's breast. However, it should be understood that vacuum system (110) may be actuated at any suitable time during the process, in addition to or in lieu of actuating vacuum system (110) before inserting needle portion (10) into the patient's breast. For instance, vacuum system (110) may be actuated after needle portion (10) is inserted into the patient's breast, before and/or after firing mechanism (90) is cocked. Vacuum system (110) may also be actuated after cutter (50) has been fired, to further assist in a severed tissue sample being drawn proximally through cutter lumen (52). Still other suitable ways in which biopsy device (2), and variations of biopsy device (2), may be operated will be apparent to those of ordinary skill in the art in view of the teachings herein. Furthermore, use of biopsy device (2) is not limited to the context of breast biopsies, let alone biopsy procedures in general.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A biopsy device operable to sever a tissue sample, the biopsy device comprising:
   (a) a body having a proximal end and a distal end, wherein the body comprises a longitudinal axis extending through the body;
   (b) a cannula extending from the distal end of the body;
   (c) a hollow cutter at least partly positioned in the cannula, the cutter defining a cutter lumen wherein the cutter is operable to sever a tissue sample;
   (d) a tip supported by the cannula, wherein the tip is configured to penetrate tissue;
   (e) a scissor grip comprising a first arm and a second arm, wherein the first arm and the second arm are pivotally connected;
   (f) a vacuum source supported by the body, wherein the vacuum source is operable to induce a vacuum in the cutter lumen, wherein the first arm and the second arm are positioned such that the vacuum source extends along the longitudinal axis of the body in between the first arm and the second arm of the scissor grip, wherein squeezing the first arm towards the second arm creates a mechanical suction in the vacuum source; and
   (g) a tissue holder removably coupled with the body and configured to receive a tissue sample severed by the cutter.

2. The biopsy device of claim 1, further comprising a handle supported by the body, wherein the handle is operable to drive the vacuum source to induce the vacuum in the cutter lumen, wherein the second arm is in communication with the handle.

3. The biopsy device of claim 2, wherein the second arm comprises a first end and a second end, wherein the second end of the second arm is pivotally attached to the vacuum source.

4. The biopsy device of claim 2, wherein the vacuum source comprises:
   (i) a cylinder defining a bore, wherein the bore has a distal end and a proximal end, wherein the bore is in fluid communication with the cutter lumen,
   (ii) a piston comprising a rod having a first end coupled with the handle and a second end having a head, wherein the head is operable to be advanced in an axial direction between the distal end and the proximal end of the bore, wherein the first end of the rod is operable to be advanced in an axial direction by the handle, and
   (iii) a spring engaged with the head of the piston, wherein the spring is configured to bias the head in an axial direction.

5. The biopsy device of claim 1, further comprising a manifold coupled with the cannula, wherein the manifold is configured to vent at least a portion of the cannula to atmospheric air.

6. The biopsy device of claim 5, wherein the cannula comprises a vent opening in fluid communication with the manifold, wherein the cutter is operable to selectively cover and uncover the vent opening of the cannula.

7. The biopsy device of claim 1, further comprising a cutter loader, wherein the cutter loader is coupled with the cutter and is operable to rotate the cutter, wherein the cutter loader comprises:
   (i) a loader body having a distal end and a proximal end, wherein the proximal end of the loader body has a trigger engagement feature,
   (ii) a rotatable ring engaged with the distal end of the loader body, and
   (iii) a resilient member coupled with the loader body, wherein the resilient member is configured to rotatingly bias the loader body.

8. The biopsy device of claim 7, further comprising a trigger coupled with the cutter loader, wherein the trigger comprises:
   (i) a lever having an upper end and a lower end, wherein the lever is rotatably attached to the body at a pivot point between the upper end and the lower end, wherein the lower end of the trigger is manually engageable by a user,
   (ii) a third arm having a proximal end and a distal end, wherein the proximal end of the third arm is operable to be engaged by the upper end of trigger, wherein the distal end of the third arm comprises a loader engagement feature configured to selectively engage with the trigger engagement feature of the loader body, and
   (iii) a resilient member configured to bias the third arm to engage the loader engagement feature with the trigger engagement feature.

9. The biopsy device of claim 8, wherein the trigger engagement feature comprises a notch, wherein the loader engagement feature comprises a tab extending transversely from the third arm.

10. The biopsy device of claim 1, wherein the cannula has a pair of longitudinal edges defining a transverse aperture, wherein the cutter comprises a longitudinal cutting edge configured to cooperate with one of the cannula longitudinal edges to shear tissue protruding into the transverse aperture.

11. A biopsy device operable to obtain at least one tissue sample, the biopsy device comprising:
   (a) a body having a longitudinal axis extending through the body;
   (b) a cannula extending from the body, wherein the cannula defines a transverse aperture and a cannula lumen, wherein the cannula comprises a vent opening in selective fluid communication with the transverse aperture;
   (c) a hollow cutter at least partly positioned in the cannula lumen, wherein the cutter defines a cutter lumen, wherein the cutter is operable to be rotated between a closed position and an open position relative to the transverse aperture of the cannula, wherein the cutter is operable to sever the at least one tissue sample from a tissue portion protruding through the transverse aperture of the cannula;
   (d) a cutter loader supported by the body, wherein the cutter loader is operable to load the cutter into the open position;
   (e) a trigger mechanism supported by the body, wherein the trigger mechanism is operable to communicate with the cutter loader to fire the cutter from the open position to the closed position;
   (f) a tissue sample holder configured to receive the at least one tissue sample from the cutter lumen;
   (g) a vacuum source supported by the body, wherein the vacuum source is operable to draw the tissue sample through the cannula lumen by applying a suction through the vent opening, wherein the vacuum source is configured to concurrently draw the tissue sample as the cutter rotates to sever the at least one tissue sample; and
   (h) a scissor grip comprising a first arm and a second arm, wherein the scissor grip is moveable from a first position to a second position when the first arm and the second arm are squeezed together to create a mechanical suction in the vacuum source, wherein the first arm and the second arm are positioned such that the vacuum source extends along the longitudinal axis of the body in between the first arm and the second arm of the scissor grip.

12. The biopsy device of claim 11, wherein the vacuum source is mechanically operable by a single hand gripping the body of the biopsy device.

13. The biopsy device of claim 11, wherein the vacuum source comprises a piston and a cylinder.

14. The biopsy device of claim 13, further comprising a handle supported by the body, wherein the handle is operable to operate the piston.

15. The biopsy device of claim 14, wherein the vacuum source is manually operable to generate a vacuum between approximately 18 inches Hg. and approximately 20 inches Hg.

16. The biopsy device of claim 11, wherein the cutter loader comprises a torsion spring, wherein the cutter loader is operable to hold the torsion spring in a stressed position, wherein the trigger mechanism is operable to release the torsion spring from the stressed position.

17. The biopsy device of claim 11, wherein the cutter is configured to cover the transverse aperture when the cutter is in the closed position.

18. A method of using a biopsy device to capture a tissue sample, wherein the biopsy device comprises a body, a needle extending from the body, wherein the needle has a transverse aperture, wherein the needle defines a needle lumen, wherein the biopsy device further comprises a hollow cutter positioned within the needle lumen, the cutter comprising a sharp edge and a flat edge, wherein the sharp edge is configured to cut tissue, a cutter loading and firing mechanism operable to load and fire the cutter relative to the transverse aperture, and a manually operable vacuum source located within the body, wherein the cutter is movable relative to the transverse aperture from a loaded position to a fired position to sever tissue protruding through the aperture, wherein the cutter defines a cutter lumen, the method comprising:
   (a) inserting the needle into a patient, wherein the cutter is in the fired position during the act of inserting;
   (b) loading the cutter from the fired position to the loaded position;
   (c) activating the cutter loading and firing mechanism to move the cutter from the loaded position to the fired position, wherein moving the cutter from the loaded position to the fired position comprises rotating the cutter such that the sharp edge rotates against tissue to capture a tissue sample; and
   (d) operating the vacuum source to draw the severed tissue sample proximally through the cutter lumen concurrently as the cutter rotates to capture a tissue sample, wherein operating the vacuum source comprises squeezing a first arm of a scissor grip towards a second arm of the scissor grip, wherein the first arm and the second arm are in communication with the vacuum source, wherein the the first arm and the second arm are positioned to straddle the vacuum source, wherein squeezing the first arm towards the second arm creates a mechanical suction within the vacuum source.

19. The method of claim 18, wherein the cutter loading and firing mechanism comprises a rotatable ring manually operable to rotate the cutter from the fired position to the loaded position, wherein the act of loading further comprises manually rotating the rotatable ring relative to the body.

20. The method of claim 18, wherein the acts of inserting the needle and operating the vacuum source are performed using one hand.

* * * * *